(12) United States Patent
Pretorius et al.

(10) Patent No.: US 8,992,435 B2
(45) Date of Patent: Mar. 31, 2015

(54) SYSTEM AND METHOD FOR CLASSIFYING A HEART SOUND

(75) Inventors: Eugene Pretorius, Kuilsrivier (ZA); Otto Marsél Strydom, Stellenbosch (ZA); Matthys Louwrens Cronje, Somerset West (ZA)

(73) Assignee: Diacoustic Medical Devices (Pty) Ltd, Stellenbosch (ZA)

( * ) Notice: Subject to any disclaimer, the term of this patent is extended or adjusted under 35 U.S.C. 154(b) by 0 days.

(21) Appl. No.: 13/821,121

(22) PCT Filed: Aug. 25, 2011

(86) PCT No.: PCT/IB2011/001938
§ 371 (c)(1),
(2), (4) Date: Mar. 6, 2013

(87) PCT Pub. No.: WO2012/025815
PCT Pub. Date: Mar. 1, 2012

(65) Prior Publication Data
US 2013/0226019 A1    Aug. 29, 2013

(30) Foreign Application Priority Data
Aug. 25, 2010    (ZA) .................................. 2010/06120

(51) Int. Cl.
| A61B 5/02 | (2006.01) |
| A61B 7/04 | (2006.01) |
| A61B 5/0452 | (2006.01) |
| A61B 5/0456 | (2006.01) |
| A61B 5/00 | (2006.01) |

(52) U.S. Cl.
CPC .................. *A61B 7/04* (2013.01); *A61B 5/0452* (2013.01); *A61B 5/0456* (2013.01); *A61B 5/7264* (2013.01); *A61B 5/7267* (2013.01)
USPC ......................................................... 600/528

(58) Field of Classification Search
None
See application file for complete search history.

(56) References Cited

U.S. PATENT DOCUMENTS

| 5,738,102 | A  | * | 4/1998 | Lemelson | ...................... | 600/483 |
| 6,572,560 | B1 |   | 6/2003 | Watrous et al. | | |
| 7,300,405 | B2 | * | 11/2007 | Guion et al. | .................. | 600/528 |
| 7,351,207 | B2 |   | 4/2008 | Priemer | | |
| 7,539,532 | B2 | * | 5/2009 | Tran | .............................. | 600/509 |
| 7,733,224 | B2 |   | 6/2010 | Tran | | |
| 2006/0198533 | A1 | * | 9/2006 | Wang et al. | ..................... | 381/67 |
| 2008/0013747 | A1 | * | 1/2008 | Tran | ................................. | 381/67 |
| 2012/0130263 | A1 | * | 5/2012 | Pretorius et al. | .............. | 600/509 |

FOREIGN PATENT DOCUMENTS

WO    WO 2011/015935    2/2011

OTHER PUBLICATIONS

Regueiro-Gomez, "A new method for automated blood pressure measurement", Physiol. Meas., 1998, vol. 19, pp. 205-212.
International Search Report for international application No. PCT/IB2011/001938, dated Dec. 6, 2011 (3 pages).

* cited by examiner

*Primary Examiner* — Brian T Gedeon
(74) *Attorney, Agent, or Firm* — Hamre, Schumann, Mueller & Larson, P.C.

(57) ABSTRACT

A method and system for electronically classifying a pre-processed heart sound signal of a patient as functional (normal) or pathological is provided. The pre-processed patient heart sound signal is segmentised and features are extracted therefrom (104) to build up a feature vector which is representative of the heart sound signal. The feature vector is then fed to a diagnostic decision support network (105) comprising a plurality of artificial neural networks, each relating to a known heart pathology, which is in turn used to conduct the classification.

5 Claims, 6 Drawing Sheets

SYSTEM AND METHOD FOR CLASSIFYING A HEART SOUND

FIELD OF THE INVENTION

This invention relates to a system and method for classifying a heart sound, more particularly for classifying a digitised acoustic heart sound so as to provide a diagnosis and differentiation between functional and pathological heart sounds.

BACKGROUND TO THE INVENTION

Cardiac auscultation refers to the process of determining cardiac well-being or illness by listening to the heart through a stethoscope. The results obtained by means of these techniques can, however, be very subjective and depend to a large extent on the experience and acquired knowledge of the diagnosing health care worker.

The majority of cardiac abnormalities manifest themselves as cardiac murmurs. However, not all murmurs are pathological. Innocent heart murmurs are sounds made by blood circulating through heart chambers and valves or blood vessels near the heart. Innocent heart murmurs are more common in children and are considered to be harmless.

Echo-cardiography is a technique which is considered by many to be one of the, if not the, most accurate aids in the field. It utilises ultrasound technology to generate visual images of the beating heart, but requires advanced training, skill and experience to manipulate the ultrasound probe in order to obtain useful images. An echo-cardiography system will, however, require an investment of close to ZAR1 Million at the time of writing, excluding costs associated with, for example, the training of staff to operate the system and meaningfully analyse the images obtained. This high cost means that echo-cardiography systems are not a feasible option for the majority of healthcare institutions in less affluent areas.

It is estimated that up to 90% of paediatric patients will exhibit some form of heart murmur on examination, although less than 1% will eventually turn out to have a congenital heart defect. Although most paediatric cardiologists can diagnose an innocent heart murmur with a very high degree of accuracy, sensitivity and specificity, even a routine paediatric cardiology evaluation is generally too costly for people from middle to low income groups.

This is particularly true in the context of a large number of developing countries, such as South Africa, where, in addition to the high cost of paediatric cardiology evaluations, patients often have to travel long distances from rural communities in order to visit one of the few paediatric cardiologists available for the population of approximately 48 million people. The referral of paediatric patients to paediatric cardiologists can therefore become extremely difficult and in most cases impractical from a logistical point of view.

When a serious congenital cardiac defect goes undetected, the physical, socio-economical and emotional damage to the patient and his or her caretakers can be enormous.

It is therefore of the utmost importance that private healthcare physicians and nurses who look after paediatric patients must be able to determine which patients will require additional evaluation as well as the urgency with which such evaluation should be conducted.

The only assistance presently available to healthcare workers to evaluate heart sounds is the common stethoscope, which can be either mechanical or electronic. Besides the rate and frequency (pitch) of the heart sounds, morphological features, which might provide an important indication of a critical heart disorder, may be undetectable by the human ear.

A low cost, portable, digital system for analysing heart sounds and making preliminary diagnoses would therefore be a very useful instrument to healthcare workers operating in the field. In order to be useful in such an automated system, recorded heart sounds must, however, be digitised and pre-processed for optimal feature extraction. Only once such pre-processing has been done will the signals be useful in a decision making network. Naturally, the more accurately features can be extracted, the more accurate the resulting diagnoses may be.

PCT patent application PCT/IB2010/001923, which is incorporated in its entirety herein by reference, discloses a medical decision support system which provides a process for pre-processing recorded heart sound signals to render them useful in decision support system. The patent application does not, however, disclose a method or system for classifying the pre-processed recorded heart sound signals to provide a diagnosis or differentiation between functional and pathological heart sounds.

OBJECT OF THE INVENTION

It is an object of this invention to provide a system and method for classifying pre-processed recorded heart sound signals to provide a diagnosis or differentiation between functional and pathological heart sounds which alleviates at least some of the abovementioned problems.

SUMMARY OF THE INVENTION

In accordance with this invention there is provided a method of classifying a pre-processed heart sound signal of a patient,
the method being characterised in that the pre-processed patient heart sound signal is electronically compared to a plurality of similarly pre-processed heart sounds corresponding to each of a plurality of pathologies and a diagnosis made by determining whether the patient heart sound corresponds to the heart sounds of any one or more of the pathologies.

Further features of the invention provide for the determination to include a confidence measure to indicate the confidence with which a diagnosis is made; and for an artificial neural network (ANN) to be provided for each pathology, each artificial neural network being trained with at least features extracted from the pre-processed heart sounds corresponding to the applicable pathology, and each artificial neural network to be used to determine whether the pre-processed patient heart sound corresponds to the pathology associated therewith.

Still further features of the invention provides for a diagnostic decision support network to be provided which comprises the artificial neural networks for each pathology, the diagnostic decision support network being used to determine if the pre-processed patient heart sound signal corresponds to the heart sounds of any one or more of the pathologies; and for the pre-processed heart sound signal to be segmentised and features are extracted therefrom, the features being compiled into a feature vector which serves as input to the diagnostic decision network.

Yet further features of the invention provide for the heart sound signal to be pre-processed by identifying or predicting locations of individual heart beats within the heart sound signal, predicting locations and durations for systole and diastole segments of the heart sound signal, compiling a peak array containing peak locations within the heart sound signal that correspond to possible locations of S1 and S2 heart sound pulses in the heart sound signal, calculating interval sizes between the peak locations in the peak array, selecting and isolating heart beats in the heart sound signal that were detected with the highest level of confidence based on the predicted durations of the systole and diastole segments of the heart sound signal and the peak array, determining if segmentation of the heart sound signal is possible based on the selected and isolated heart beats, dividing inter-peak intervals that make up the heart sound signal into even and odd groups in the order in which they appear if segmentation of the heart sound signal was found to be possible, and calculating the variance and mean for both groups and taking the group with the largest ratio of variance over mean as corresponding to the diastole intervals and the other group as corresponding to the systole intervals.

The invention also provides a system for classifying a pre-processed heart sound signal of a patient, the system including a processor configured to compare the pre-processed patient heart sound to a plurality of similarly pre-processed heart sounds corresponding to each of a plurality of pathologies and to provide a diagnosis by determining whether the patient heart sound signal corresponds to the heart sounds of any one or more of the pathologies.

Further features of the invention provide for the processor to be further configured to calculate a confidence measure indicative of the confidence with which a diagnosis is made; for the system to include a diagnostic decision support network comprising an artificial neural network associated with each pathology, the artificial neural networks being trained with at least features extracted from the pre-processed heart sounds associated with its pathology and the processor being further configured to use the diagnostic decision support network to provide the diagnosis; and for the processor to be further configured to segmentise the heart sound signal and to extract features therefrom, and to compile the features into a feature vector which serves as input to the diagnostic decision network.

BRIEF DESCRIPTION OF THE DRAWINGS

The invention will now be described, by way of example only with reference to the accompanying representations in which.

DETAILED DESCRIPTION WITH REFERENCE TO THE DRAWINGS

Figure 1:
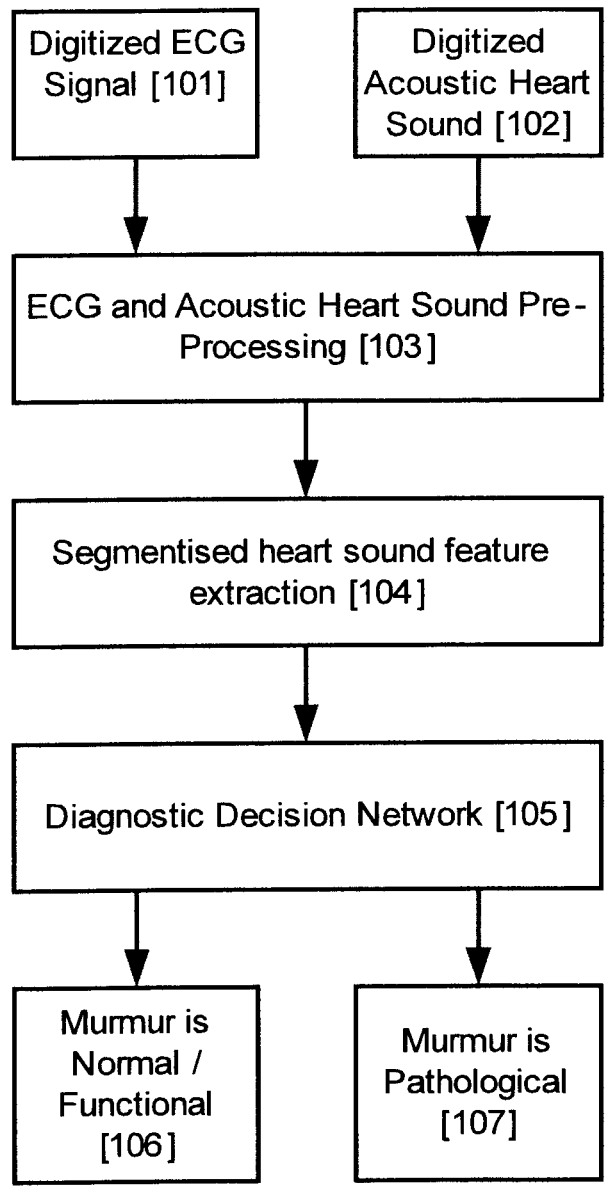
FIG. 1 is flow diagram for a system for classifying a heart sound signal of a patient.

To enable an automated system to distinguish between pathological and normal heart murmurs an acoustic heart sound signal (102) and its associated ECG (101) signal must be digitised and pre-processed (103) for optimal feature extraction (104) for input into a support decision network (105) as shown in FIG. 1. It is with this feature extraction from the segmented heart sound recording (104) and decision support network (105) that the current invention is concerned.

The means for receiving the digitized acoustic heart sound at step (102) may include an electronic stethoscope placed on the chest of the subject, analogue circuitry including amplifiers, analogue filters and an analogue-to-digital converter.

Likewise, the means for receiving the digitised ECG signal at a step (101) may include three ECG leads with ECG electrodes connected to it, an analogue differential amplifier with a feedback line, analogue filters and an analogue-to-digital converter.

Figure 2:
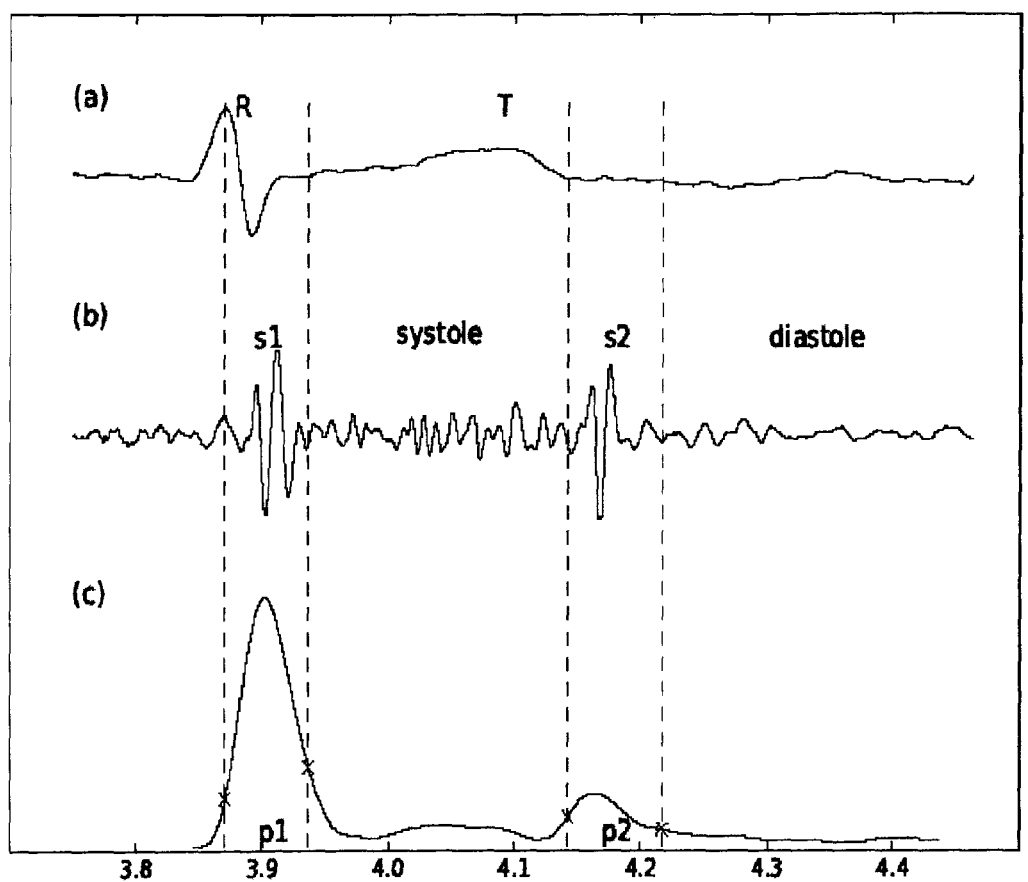
FIG. 2 is patient heart signal including (a) an ECG reference signal with R-T peaks start and end systole region, (b) a single cardiac cycle with S1 and S3 components segmented with an ASD murmur, and (c) an envelope of a beat used to find the S1 and S2 regions.

PCT patent application PCT/IB2010/001923 describes in detail the pre-processing of heart sounds. In brief, however, the pre-processing of the digitized acoustic heart sound and digitised ECG signal at step (103) includes the steps of digitally filtering the respective signals, determining the presence of an acoustic heart sound and ECG signals, locating the positions of the S1 and S2 heart sounds within the respective heart beats that make up the heart sound signal, locating the QRS peak within the respective ECG periods and parsing the recorded digitized acoustic heart sound within its respective heart beat cycles as illustrated in FIG. 2.

At step (104), the heart beat cycles are then segmented and specific features are extracted from them. As shown in more detail in FIG. 3, the segmentation includes the division of the heart beat cycles into a predetermined number of segments (a, b, c, d, e and f) for each of which a power spectrum is then calculated and features extracted from a Shannon envelope of the signal. The features are extracted from the Shannon envelope at predetermined time indexes so as to be representative of the beats making up the signal. From these specific feature points a feature vector is compiled and serves as input to a diagnostic decision support network shown at step (105).

According to the invention, the diagnostic decision support network shown at step (105) is implemented by means of a neural network which indicates that the input heart sound is either normal, at step (106), or contains a murmur associated with a predefined pathology, at step (107). From the neural network's output, signal quality and segmentation steps a confidence factor is also calculated to indicate the confidence with which the final decision was made.

Figure 3:
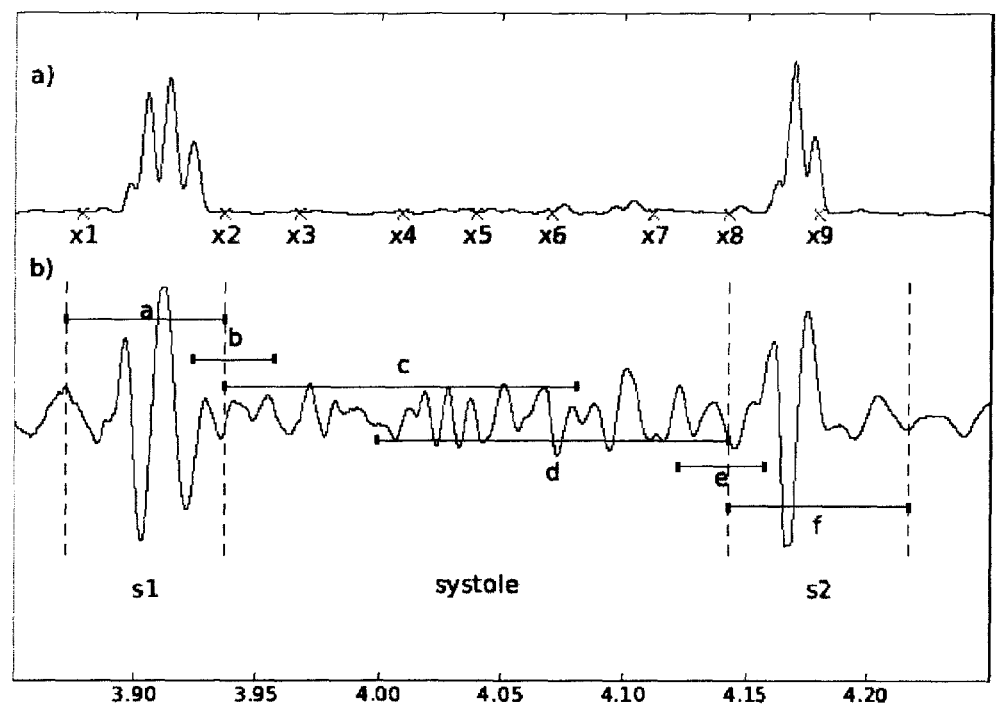
FIG. 3 is (a) a Shannon envelope for a patient heart signal and time indexes used for features calculation and (b) SIFT segments time division of a signal.
Figure 4:
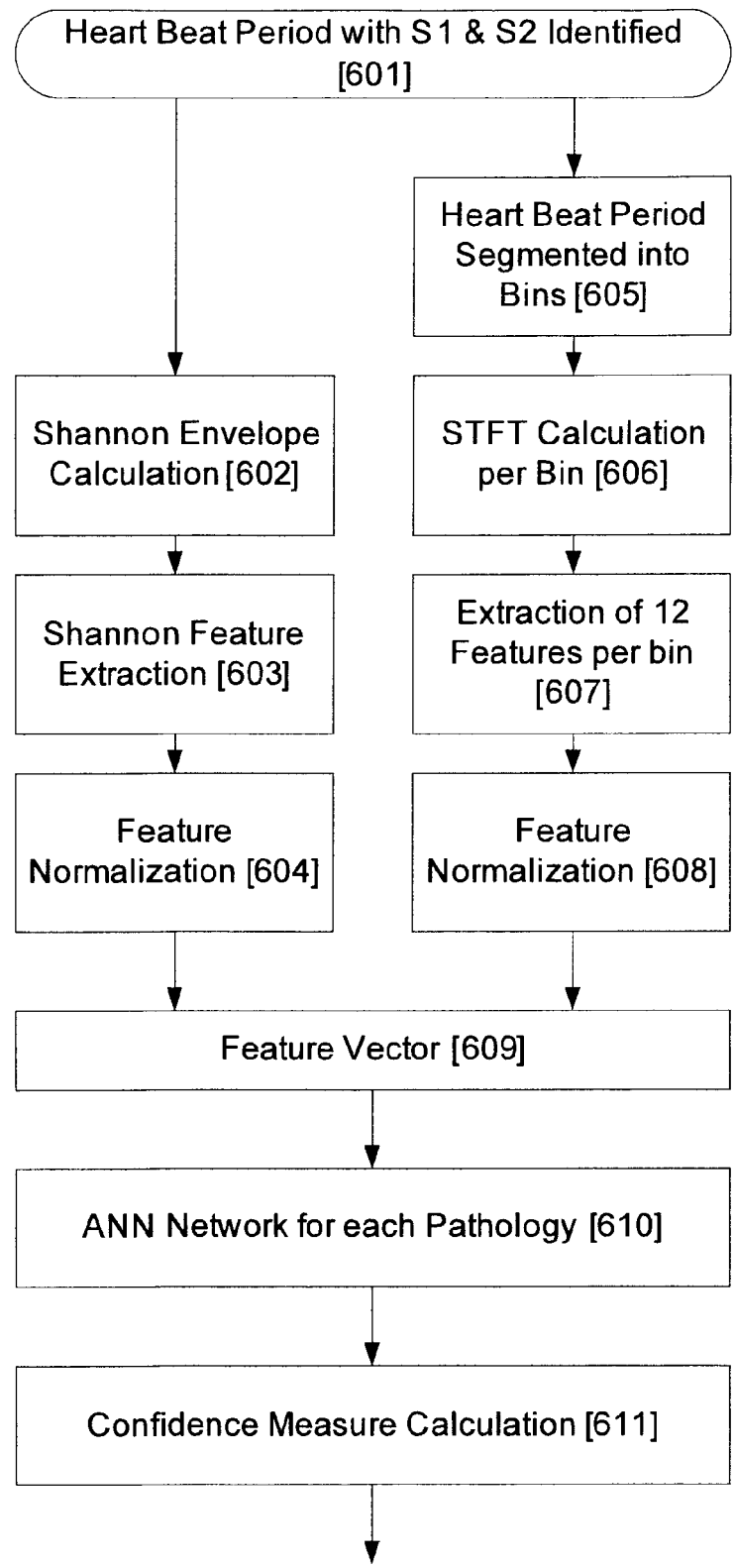
FIG. 4 is a flow diagram of the classification process of a recorded heart sound.

The steps of segmenting the pre-processed heart sound and conducting the feature extraction (104) are exemplified in more detail by the flow diagram shown in FIG. 4. The Shannon envelope is calculated at step (602) from the heart beat periods with S1 and S2 identified (during pre-processing of the heart sound signal) at (601). Eight Shannon envelope components (features) are then extracted from the Shannon envelope at (603). These components are illustrated in FIG. 3 as time indexes. These time indexes, shown as x2 to x9 are positioned at times 0.1, 0.15, 0.35, 0.5, 0.65, 0.85 in the systole region of the heat beat and at times 0 and 0.5 in the S2 region. The envelope's mean values in these regions are then calculated and normalized by scaling the resulting 8 feature points to have a maximum value of 1, at step (604).

From the said heart beat periods (601) the identified S1 and S2 sounds, as well as the systole region, are segmented into bins (a to f) at (605), as shown in more detail in signal (b) of FIG. 3. The Short-Time Fourier Transform ("STFT") is calculated for the overlapping bins a, b, c, d, e and f at (606). The STFT is split into low frequencies (LF), 20-150 Hz and high frequencies (HF) 150-420 Hz. 12 values, 4 LF and 8 HF values are then extracted from the 6 bin segments spanning the entire S1, systole and S2 region at (607). The HF values are scaled to the same magnitude as the LF values to enable the detection of soft murmurs. The feature set is normalized limiting the range to [−1;1] at (608). The high frequency components of segments a and b are removed as well as 2 LF components of segment b, reducing the feature vector to 54 values. The number of values in the feature vector is therefore calculated as follows:

6 regions*(8HF+4LF)=72

72−(8HF+8LF)=56

56−(2bLF)=54

Figure 5:
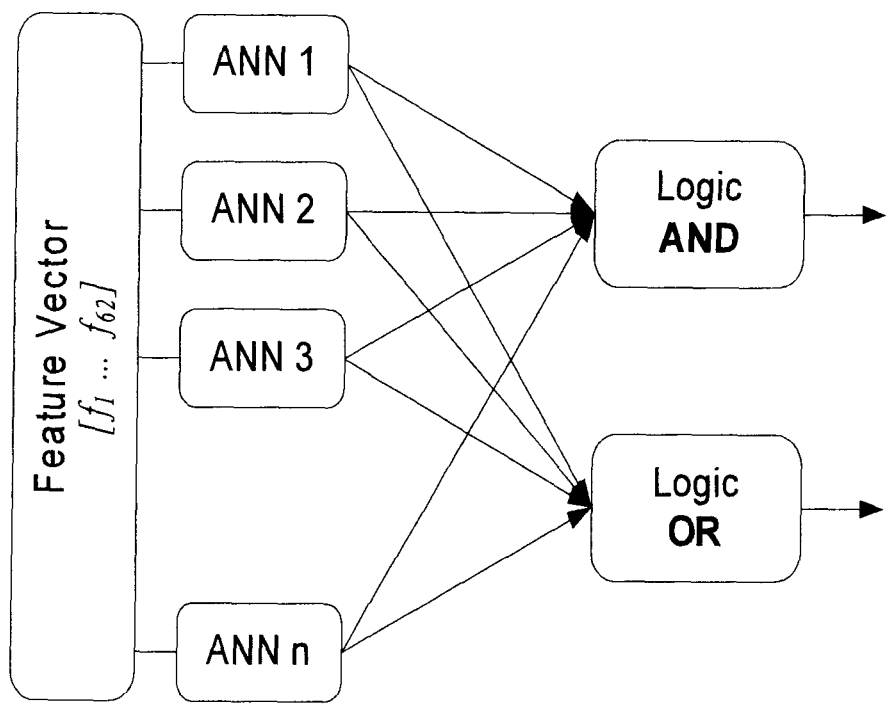
FIG. 5 is a classification model using artificial neural networks to identify specific murmur types.
Figure 6:
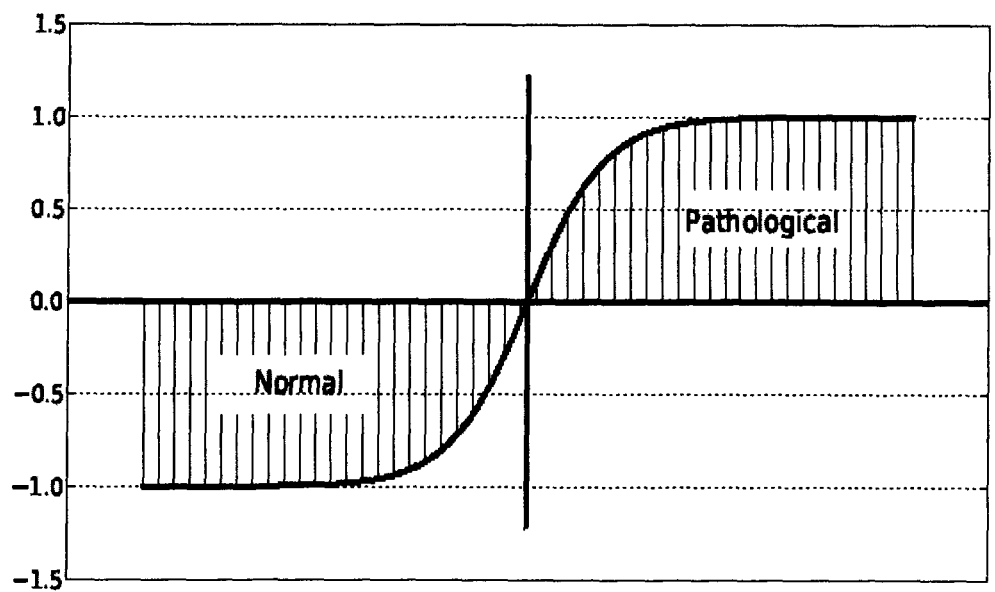
FIG. 6 is a tanh transfer function used in the classification system.

The 62 point feature vector thus calculated at (609), consisting of the Shannon and STFT features, is then fed into a network of artificial neural networks (ANNs) at (610). The network is shown in more detail in FIG. 5. Each ANN (shown as "ANN 1" to "ANN n") in the network represents a specific pathology. An ANN is created for each pathology and is trained with features extracted from heart sounds representative of that specific pathology, as well as with features from normal heart sounds. A tanh transfer function is used on each of the network outputs limiting the range to [−1;1], as shown in FIG. 6. Each output of the above-mentioned ANNs is used to determine if the analysed heart beats of a recorded heart sound contains a pathological murmur. The confidence with which this decision is made is also calculated at (611).

Figure 7:
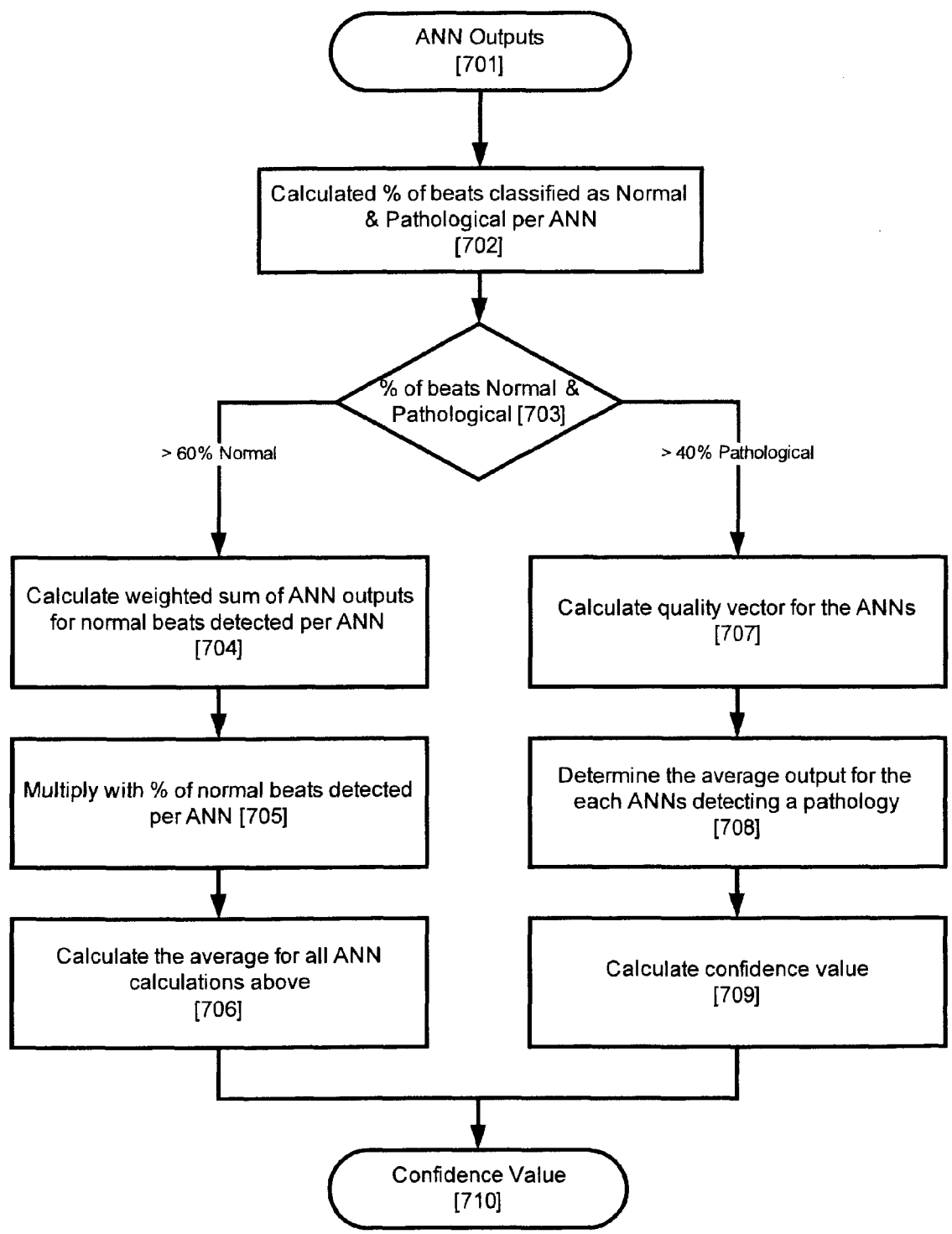
FIG. 7 is a flow diagram of diagnosis and confidence measure calculation.

FIG. 7 illustrates the process used to analyse each ANN's outputs to determine if a heart sound contains a pathological murmur as well as to determine the confidence with which this decision is made. For each heart beat analysed, each ANN's output (701) within the ensemble of ANNs is used to calculate the percentage of beats classified as normal and the percentage classified as pathological in a recorded signal. A single beat is classified as normal if all ANN outputs specify the beat as normal and pathological if one or more of the ANN outputs classify it as pathological at (702). For a complete heart sound recording to be classified as normal all ANNs within the ensemble of ANNs must classify at least 60% of the beats making up the signal as normal (60% of the beats were below the ANN output threshold). If at least one ANN within the ensemble of ANNs classifies more than 40% of the beats making up the recorded signal as pathological, the heart sound as a whole is classified as pathological (in other words 40% or more of the beats where above the threshold) (703).

Each ANN in the network classifies all selected beats from a recording. Their outputs are limited in the range [−1, 1] corresponding to [normal; pathological]. Values in between are considered uncertain or badly correlated with the training set. The confidence measurement is a weighted sum of the ANN's outputs, where the weight is calculated as the percentage of beats matching the signal classification.

If a signal is classified as normal only those beats that contributed to a normal classification are considered. To calculate the confidence measure for a normal acoustic heart recording the average output for the selected beats at the input that was detected as normal is determined for each ANN output (704). The average ANN output for each ANN is then multiplied with the percentage of normal heart beats detected by the specific ANN (705) and these values are then used to calculate the average confidence for all the ANN outputs (706).

To calculate a confidence measure for a pathological acoustic heart recording, a quality vector is determined based on the statistical results obtained from the accuracy testing of each network, therefore assigning a quality value to each ANN calculated according to the ANN's accuracy (707). If more than one ANN in the ensemble of ANNs detects a pathology, the quality value used is increased accordingly. For each ANN that detects a pathology, the average output for the selected beats at the input that were detected as pathological is calculated (708). If a single ANN determined the recorded acoustic heart sound as normal, the confidence with which it is done is determined, the same method as specified in the steps above (704, 705, 706) is used. To determine the final confidence value with which a pathological acoustic heart sound recording was identified, the average of the ANN outputs is added to the quality number (determined from the quality vector) and the confidence value of the ANNs that detected the heart sound as normal is subtracted (709).

It will be appreciated that many other methods of classifying a heart sound signal of a patient exist which fall within the scope of the invention, particularly in the manner in which the heart sound signal is pre-processed and compared to similarly pre-processed heart sound signals associated with pathologies.

Similarly, the system for classifying a heart sound signal of a patient can have any suitable configuration and need not rely on ANNs. It will further be appreciated that the processor used to implement the system can be a single device, such as a computer, or multiple devices in a cooperative arrangement. Where ANNs are used they can have any suitable configuration.

The invention claimed is:
1. A method of classifying a recorded, digitized acoustic heart sound signal of a patient, the method being performed by a processor and comprising the steps of:
pre-processing the heart sound signal so as to be parsed into respective heart beat cycles by identifying or predicting locations of individual heart beats within the heart sound signal, predicting locations and durations for systole and diastole segments of the heart sound signal, compiling a peak array containing peak locations within the heart sound signal that correspond to possible locations of S1 and S2 heart sound pulses in the heart sound signal, calculating interval sizes between the peak locations in the peak array, selecting and isolating heart beats in the heart sound signal that were detected with the highest level of confidence based on the predicted durations of the systole and diastole segments of the heart sound signal and the peak array, determining if segmentation of the heart sound signal is possible based on the selected and isolated heart beats, dividing inter-peak intervals that make up the heart sound signal into even and odd groups in the order in which they appear if segmentation of the heart sound signal was found to be possible, and calculating the variance and mean for both groups and taking the group with the largest ratio of variance over mean as corresponding to the diastole intervals and the other group as corresponding to the systole intervals;
electronically comparing the recorded pre-processed heart sound signal to a plurality of artificial neural networks, each artificial neural network being associated with a specific pathology and being trained with at least features extracted from similarly pre-processed heart sound signals with the specific pathology;
determining whether the recorded pre-processed heart sound signal corresponds to the artificial neural network associated with any one or more of the pathologies; and
classifying the recorded pre-processed heart sound signal as relating to one or more of the pathologies according to the determination.

2. A method as claimed in claim 1 wherein determining whether the recorded pre-processed heart sound signal corresponds to the artificial neural network associated with any one or more of the pathologies includes determining a confidence measure to indicate the confidence with which a diagnosis is made.

3. A method as claimed in claim 1 wherein each artificial neural network is used to determine whether the recorded pre-processed patient heart sound signal corresponds to the pathology associated therewith.

4. A method as claimed in claim 1 wherein a diagnostic decision support network is provided which comprises the artificial neural networks for each pathology, the diagnostic decision support network being used to determine if the recorded pre-processed patient heart sound signal corresponds to the artificial neural networks of any one or more of the pathologies.

5. A method as claimed in claim 4 which includes the step of segmenting the recorded pre-processed heart sound signal and extracting features therefrom, the features being compiled into a feature vector which serves as an input to the diagnostic decision network.

* * * * *